(12) United States Patent
Spiller et al.

(10) Patent No.: US 12,280,016 B2
(45) Date of Patent: Apr. 22, 2025

(54) UTILIZING THE INNATE IMMUNE SYSTEM TO DELIVER THERAPEUTIC AGENTS

(71) Applicant: Drexel University, Philadelphia, PA (US)

(72) Inventors: Kara L. Spiller, Glenside, PA (US); Kathryn L Wofford, Philadelphia, PA (US)

(73) Assignee: Drexel University, Philadelphia, PA (US)

( * ) Notice: Subject to any disclaimer, the term of this patent is extended or adjusted under 35 U.S.C. 154(b) by 389 days.

(21) Appl. No.: 17/651,673

(22) Filed: Feb. 18, 2022

(65) Prior Publication Data

US 2022/0168340 A1    Jun. 2, 2022

Related U.S. Application Data

(63) Continuation of application No. 16/615,997, filed as application No. PCT/US2018/034906 on May 29, 2018, now abandoned.

(60) Provisional application No. 62/512,284, filed on May 30, 2017.

(51) Int. Cl.
*A61K 9/16* (2006.01)
*A61K 31/573* (2006.01)
*A61K 39/00* (2006.01)

(52) U.S. Cl.
CPC .......... *A61K 9/1647* (2013.01); *A61K 31/573* (2013.01); *A61K 39/4614* (2023.05); *A61K 39/4622* (2023.05); *A61K 39/46432* (2023.05)

(58) Field of Classification Search
None
See application file for complete search history.

(56) References Cited

U.S. PATENT DOCUMENTS 9,943,481 B2    4/2018  Golomb
2015/0079155 A1*  3/2015  Jensen ............... A61P 31/14
                                                424/277.1

OTHER PUBLICATIONS

International Search Report and Written Opinion, International Patent Application No. PCT/US2018/034906, Oct. 30, 2018.
NIH, "Drug Record, Corticosteroids", https://livertox.nih.gov/Corticosteroids.htm, May 30, 2014, 1-14.
Bernal, L. , et al., "Evaluation of a nanotechnology-based approach to induce gene-expression in human THP-1 macrophages under inflammatory conditions", Immunobiology 222, 2017, 399-408.
Förster, C. , et al., "Glucocorticoid effects on mouse microvascular endothelial barrier permeability are brain specific", J Physiol 573.2, 2006, 413-425.
Gao, W. , et al., "Liposome-like Nanostructures for Drug Delivery", J Mater Chem B Mater Biol Med., Dec. 28, 2013, 1-35.

(Continued)

*Primary Examiner* — Daniel C Gamett
(74) *Attorney, Agent, or Firm* — Saul Ewing LLP; Kathryn Doyle; Justin Crotty

(57) ABSTRACT

In one aspect, the invention provides a composition comprising at least one monocyte comprising an agent that increases monocyte homing to a site of injury, and an effective amount of a drug. In another aspect, the invention provides a method of using the composition to deliver a drug to a site of injury.

12 Claims, 15 Drawing Sheets

(56) References Cited

OTHER PUBLICATIONS

Guedj, A., et al., "Preparation, characterization, and safety evaluation of poly(lactide-co-glycolide) nanoparticles for protein delivery into macrophages", International Journal of Nanomedicine 10, Sep. 23, 2015, 5965-5979.

Kelly, C., et al., "Targeted liposomal drug delivery to monocytes and macrophages", Journal of Drug Delivery, 2011, 1-11.

Klyachko, N. L., "Macrophages offer a paradigm switch for CNS delivery of therapeutic proteins", Nanomedicine (Lond)., Jul. 9, 2014, 1403-1422.

Penton-Rol, G., et al., "Up-Regulation of CCR2 Chemokine Receptor Expression and Increased Susceptibility to the Multitropic HIV Strain 89.6 in Monocytes Exposed to Glucocorticoid Hormones", J Immunol 163, 1999, 3524-3529.

Previti, M., et al., "Dexamethasone diminishes the pro-inflammatory and cytotoxic effects of amyloid β-protein in cerebrovascular smooth muscle cells", Journal of Neuroinflammation 3:18, 2006, 1-8.

Saiyed, Z. M., et al., "Magnetic nanoformulation of azidothymidine 5'-triphosphate for targeted delivery across the blood-brain barrier", International Journal of Nanomedicine 5, Apr. 7, 2010, 157-166.

Thulasiramaraju, T. V., et al., "Liposomes: A Novel Drug Delivery System", International Journal of Biopharmaceutic 3(1), 2012, 5-16.

Tong, H., et al., "Monocyte Trafficking, Engraftment, and Delivery of Nanoparticles and an Exogenous Gene into the Acutely Inflamed Brain Tissue—Evaluations on Monocyte-Based Delivery System for the Central Nervous System", PLOS ONE, Apr. 26, 2016, 1-21.

Lee, S., "Monocytes: a novel drug delivery system targeting atherosclerosis", 2014, Journal of Drug Targeting, vol. 22, issue 2, pp. 138-145.

\* cited by examiner

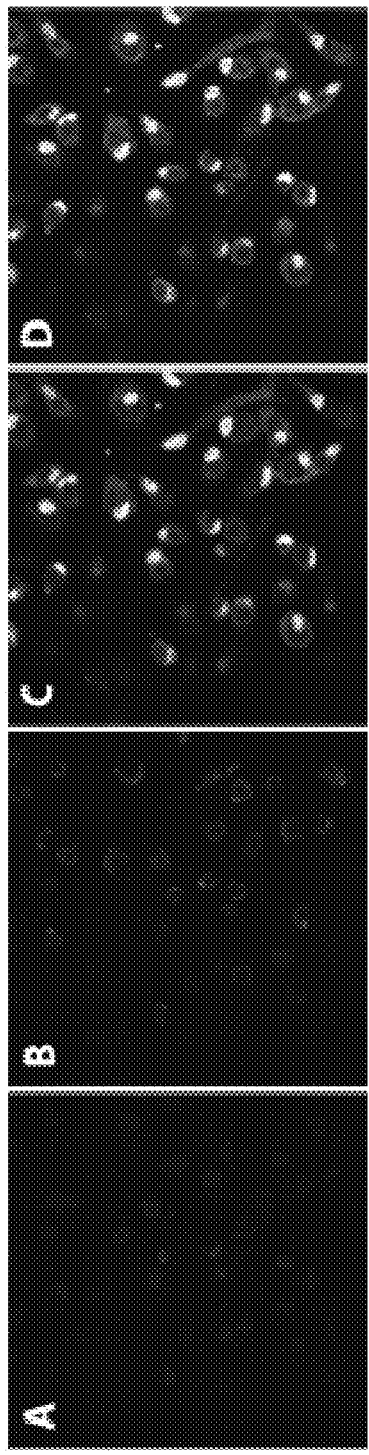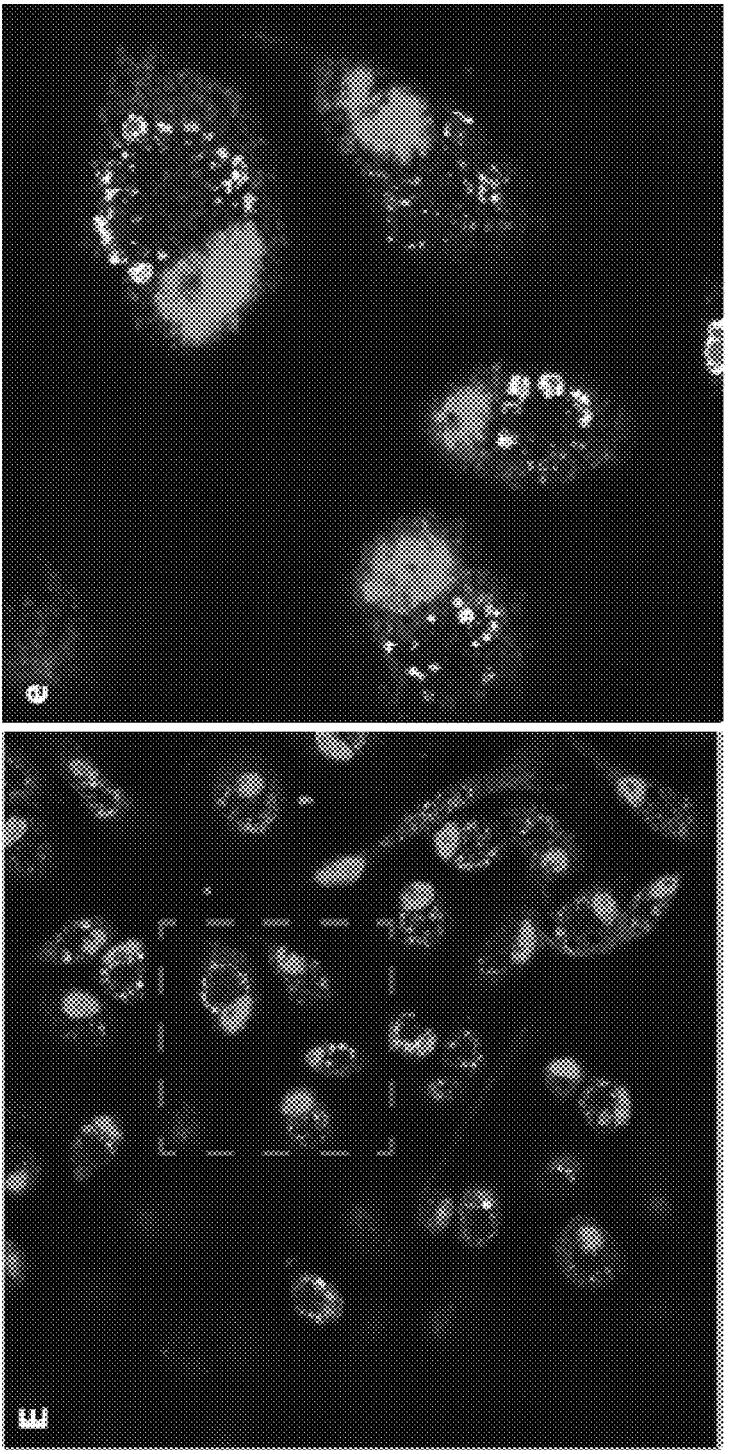

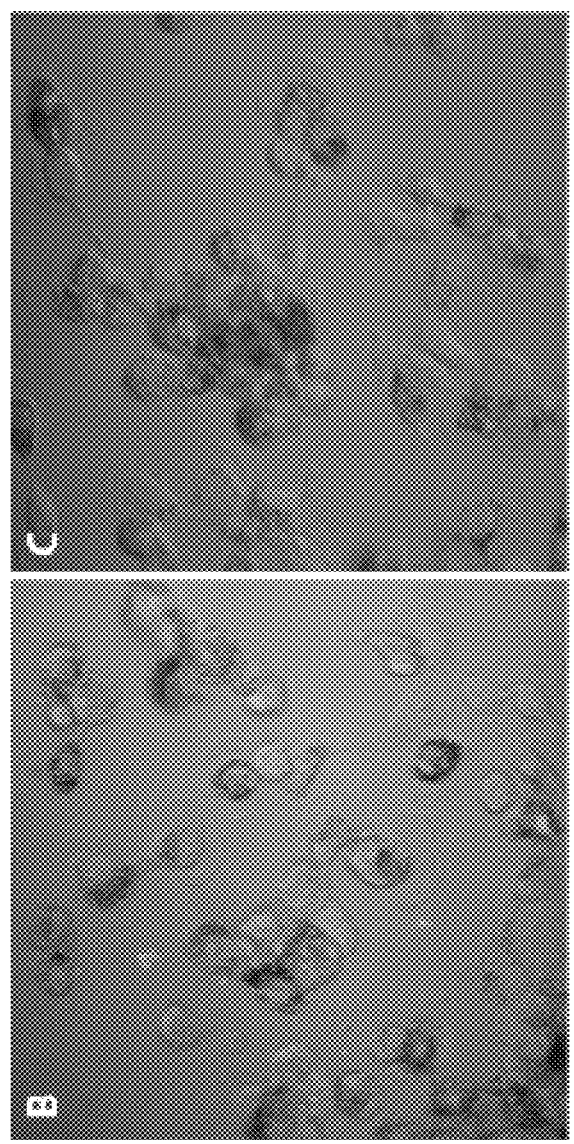
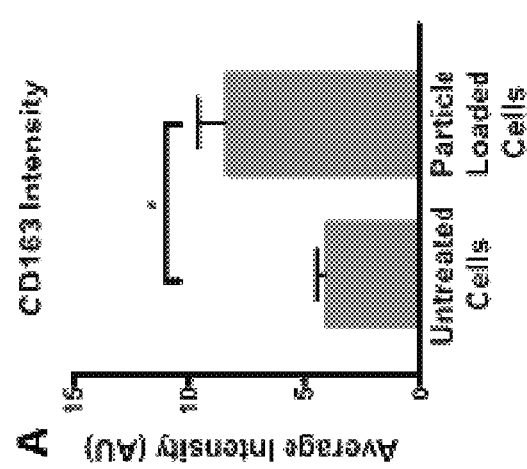
FIG. 9

UTILIZING THE INNATE IMMUNE SYSTEM TO DELIVER THERAPEUTIC AGENTS

CROSS-REFERENCE TO RELATED APPLICATIONS

This application is a continuation under 35 U.S.C. § 120 of U.S. patent application Ser. No. 16/615,997, filed Nov. 22, 2019 which is a national phase application under 35 U.S.C. § 371 of International Patent Application No. PCT/US2018/034906, filed May 29, 2018, which claims priority to U.S. Provisional Patent Application No. 62/512,284, filed May 30, 2017 and which are incorporated herein by reference in their entirety.

STATEMENT REGARDING FEDERALLY SPONSORED RESEARCH OR DEVELOPMENT

This invention was made with government support under Contract No. R01 HL130037 awarded by the National Heart, Lung, and Blood Institute (NHLBI) of the National Institutes of Health (NIH). The government has certain rights in the invention.

BACKGROUND OF THE INVENTION

Efficient drug delivery to a specific site of injury within a region of the body of the patient in order to minimize off-target effects is a continuing challenge in the pharmaceutical arts. This is especially challenging in regions of the body, such as the brain, to which access is highly regulated by endogenous systems. There is a need in the art for compositions and methods that facilitate the delivery of therapeutic agents to difficult-to-target sites of injury.

SUMMARY OF THE INVENTION

In one aspect, the invention provides a composition comprising at least one monocyte comprising an agent that increases monocyte homing to a site of injury, and an effective amount of a drug.

In another aspect, the invention provides a method of delivering a drug to a site of injury of a patient comprising administering to the patient a composition comprising at least one monocyte comprising an agent that increases monocyte homing, and an effective amount of a drug, wherein the at least one monocyte travels to the site of injury where the drug is released from the intracellular space, thereby delivering the effective amount of the drug to the site of injury.

In various embodiments, the agent that increases monocyte homing is a CCR2 modulator.

In various embodiments, the agent that increases monocyte homing is dexamethasone.

In various embodiments, one or more of the agent and the drug are localized within one or more particles within the monocyte. In various embodiments, the particle has a cross-sectional dimension between 1 nm and 50 µm.

In various embodiments, the agent and the drug are both co-localized within one or more particles within the monocyte. In various embodiments, the particle has a cross-sectional dimension between 1 nm to 50 µm.

In various embodiments, the drug is a drug that affects monocyte or macrophage behavior and may be the same or different than the agent that increases monocyte homing to a site of injury. In various embodiments, the drug that affects monocyte or macrophage behavior is interleukin-4, interleukin-10, interferon-γ or dexamethasone. In various embodiments, the drug is a drug that affects liver function or health. In various embodiments, the particle comprises a cationic polymer.

In various embodiments, the particle comprises a targeting ligand. In various embodiments, the targeting ligand promotes selective uptake by an endogenous monocyte.

In various embodiments, the particle comprises a molecule that enhances endosomal escape.

In various embodiments, the particle comprises a fluorescent dye. In various embodiments, the fluorescent dye is Nile red or Cy5.

In various embodiments, wherein the particle comprises a hydrophobic polymer core. In various embodiments, the hydrophobic polymer core comprises a poly(lactic-co-glycolic acid).

In various embodiments, the particle further comprises a coating.

In various embodiments, the particle is a phospholipid vesicle and the phospholipid vesicle comprises one or more concentric lipid layers.

In various embodiments, the drug is released from the intracellular space by monocyte-to-macrophage differentiation or an injury-specific biological cue.

In various embodiments, the drug is a prodrug that masks a functional agent and the functional agent is released at the site of injury.

In various embodiments, the site of injury is in the brain of the patient.

In various embodiments, the injury is a traumatic brain injury.

In various embodiments, the injury is a lesion caused by a synucleopathic disease.

In various embodiments, the synucleopathic disease is Parkinson's disease or dementia with Lewy bodies.

In various embodiments, the injury is a lesion caused by an amyloid-β-mediated disease.

In various embodiments, the amyloid-β mediated-disease is Alzheimer's disease.

In various embodiments, the drug affects blood-brain barrier integrity or function. In various embodiments, the drug is methylene blue, mannitol, bradykinin, or serotonin. In various embodiments, the drug promotes neuronal health or stability. In various embodiments, the drug is P7C3, a brain-derived neurotrophic factor, a nerve growth factor, a calpain inhibitor, or a flavonoid.

In various embodiments, the drug is localized to a particle and the particle comprises iron oxide and a magnetic field is applied to the site of injury, thereby promoting monocyte homing to the site of injury.

In various embodiments, the drug is localized to a particle and the particle is a capsule and the drug is contained within the capsule and ultrasound is applied to the sight of injury, thereby rupturing the capsule.

In various embodiments, the particle occupies the intracellular space of the monocyte.

In various embodiments, the particle attaches to the surface of the monocyte.

In another aspect, the invention provides a method of delivering a drug to the site of an injury in a patient comprising administering to the patient at least an agent that increases monocyte homing, and an effective amount of a drug, wherein the agent and the drug enter or attach to at least one monocyte, the endogenous monocyte travels to the site of injury in the patient; and the drug is released from the monocyte, thereby delivering the effective amount of the drug to the site of injury.

In various embodiments, the at least one monocyte is an endogenous monocyte. In various embodiments, the at least one monocyte is an exogenous monocyte. In various embodiments, one or more of the agent and the drug are localized within one or more particles within the monocyte. In various embodiments, the agent and the drug are both co-localized within one or more particles within the monocyte.

In another aspect, the invention provides a composition comprising at least one monocyte comprising an effective amount of a drug.

In another aspect, the invention provides a method of delivering a drug to a site of injury of a patient comprising administering to the patient a composition comprising at least one monocyte comprising an effective amount of a drug, wherein the drug is released from the intracellular space of the at least one monocyte at the site of injury, thereby delivering the effective amount of the drug to the site of injury.

In various embodiments, the composition is delivered locally at the site of injury.

In various embodiments, the composition is delivered systemically.

In various embodiments, the drug is localized within one or more particles within the monocyte.

In various embodiments, the particle has a cross-sectional dimension between 1 nm and 50 μm.

In various embodiments, the drug is a drug that affects liver function or health.

In various embodiments, the particle comprises a cationic polymer.

In various embodiments, the particle comprises a targeting ligand.

In various embodiments, the targeting ligand promotes selective uptake by an endogenous monocyte.

In various embodiments, the particle comprises a molecule that enhances endosomal escape.

In various embodiments, the particle comprises a fluorescent dye.

In various embodiments, the fluorescent dye is Nile red or Cy5.

In various embodiments, the particle comprises a hydrophobic polymer core.

In various embodiments, the hydrophobic polymer core comprises a poly(lactic-co-glycolic acid).

In various embodiments, the particle further comprises a coating.

In various embodiments, the particle is a phospholipid vesicle and the phospholipid vesicle comprises one or more concentric lipid layers.

In various embodiments, the drug is released from the intracellular space by monocyte-to-macrophage differentiation or an injury-specific biological cue.

In various embodiments, the drug is a prodrug that masks a functional agent and the functional agent is released at the site of injury.

In various embodiments, the site of injury is in the brain of the patient.

In various embodiments, the injury is a traumatic brain injury.

In various embodiments, the injury is a lesion caused by a synucleopathic disease.

In various embodiments, the synucleopathic disease is Parkinson's disease or dementia with Lewy bodies.

In various embodiments, the injury is a lesion caused by an amyloid-β-mediated disease.

In various embodiments, the amyloid-β mediated-disease is Alzheimer's disease.

In various embodiments, the drug affects blood-brain barrier integrity or function.

In various embodiments, the drug is methylene blue, mannitol, bradykinin, or serotonin.

In various embodiments, the drug promotes neuronal health or stability.

In various embodiments, the drug is P7C3, a brain-derived neurotrophic factor, a nerve growth factor, a calpain inhibitor, or a flavonoid.

In various embodiments, the drug is localized to a particle and the particle comprises iron oxide and a magnetic field is applied to the site of injury, thereby promoting monocyte homing to the site of injury.

In various embodiments, the drug is localized to a particle and the particle is a capsule and the drug is contained within the capsule and further comprising the application of ultrasound to the sight of injury, thereby rupturing the capsule.

In various embodiments, the particle occupies the intracellular space of the monocyte.

In various embodiments, the particle attaches to the surface of the monocyte.

BRIEF DESCRIPTION OF THE DRAWINGS

For a fuller understanding of the nature and desired objects of the present invention, reference is made to the following detailed description taken in conjunction with the accompanying drawing figure(s) wherein like reference characters denote corresponding parts throughout the several views.

FIGS. 5A-5E depict immunocytochemistry for nuclei (DAPI, A) particles (TRITC, B), the cytoplasmic glucocortiocoid receptor (BuGR2, FIG. 5C), and the overlay of the channels (FIG. 5D). Images were pseudocolored to show BuGR2, TRITC, and co-localization of the two signals as white pixels (FIGS. 5E and 5F).

FIG. 9 depicts that surface staining of CD163 is increased in cells five days after being treated with DEX particles. Data is presented as mean+/−SEM. Data was analyzed with an unpaired t-test with Welsh's correction to account for potentially inconsistent variance. The experimental group was significantly different from control group p=0.027.

DEFINITIONS

Figure 1:
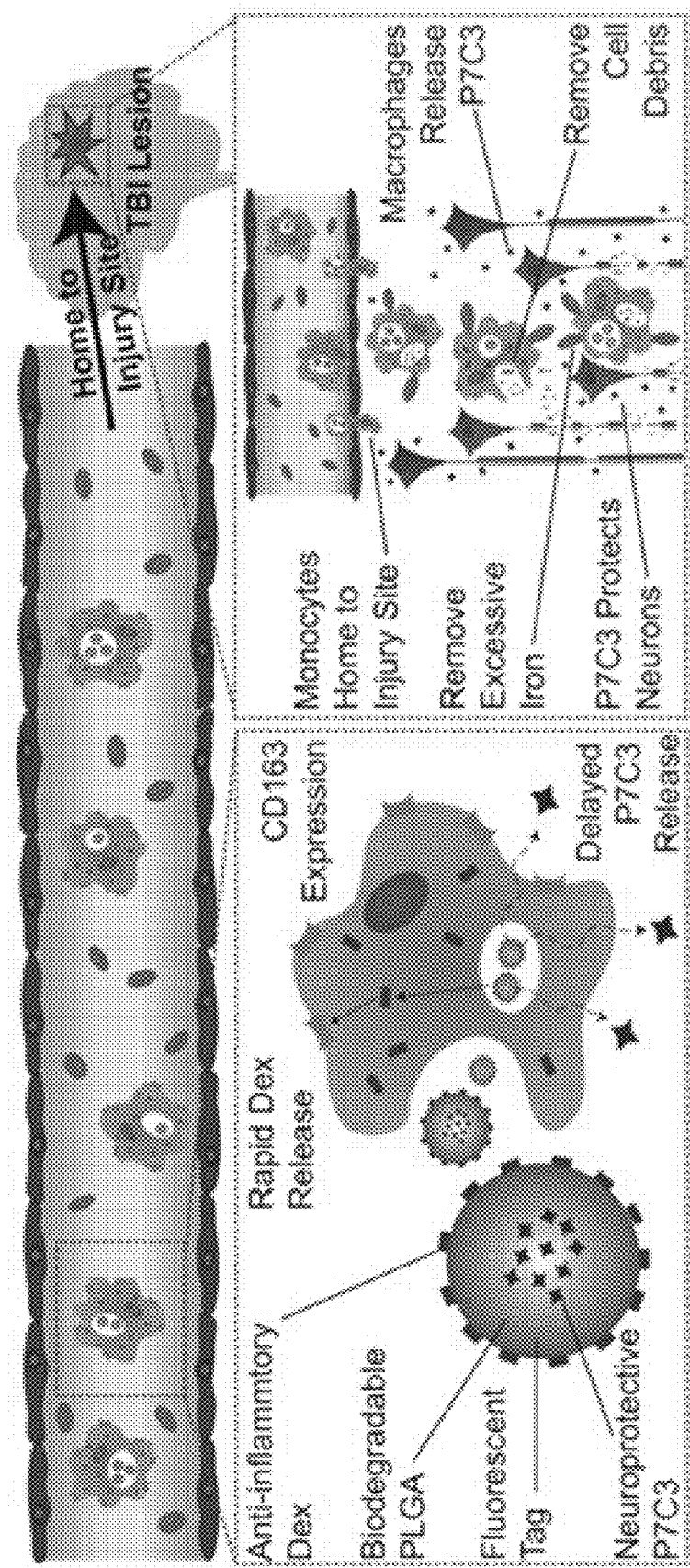
FIG. 1 depicts a schematic summarizing one embodiment of the invention in which fluorescently-labeled poly(lactic-co-glycolic acid) (PLGA) nanoparticles contain anti-inflammatory dexamethasone (dex) as well as neuroprotective drug (e.g., P7C3) and are intravenously administered after TBI. Circulating monocytes quickly phagocytose nanoparticles. Dex acts within the cell and stimulates CD163 expression. CD163-expressing monocytes home to the brain and transport their P7C3 cargo to the site of injury. Delayed P7C3 release protects neurons from mitochondrial dysfunction and axonal degeneration; CD163 removes pathological iron; and macrophages promote healthy clearance of cellular debris.

The instant invention is most clearly understood with reference to the following definitions.

As used herein, the singular form "a," "an," and "the" include plural references unless the context clearly dictates otherwise.

Unless specifically stated or obvious from context, as used herein, the term "about" is understood as within a range of normal tolerance in the art, for example within 2 standard deviations of the mean. "About" can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

As used in the specification and claims, the terms "comprises," "comprising," "containing," "having," and the like can have the meaning ascribed to them in U.S. patent law and can mean "includes," "including," and the like.

As used herein, the term "monocyte" means cells with the potential to differentiate into macrophages.

As used herein, the term "particle" means any biologically compatible structure, typically a nanoparticle or microparticle that may be phagocytosed by a monocyte and carried along with the monocyte as it migrates through the body. The term places no restriction on composition or geometry beyond this functional requirement. Particles may assembled and/or aggregated, e.g., through covalent, physical, and/or ionic bonds. Particles may include but are not limited to hydrophobic or hydrophilic, charged or uncharged polymers, metals such as gold or iron, liposomes, vesicles, and carbon structures such as nanotubes or nanodiamonds.

As used herein, the term "localized" encompasses any type of attachment to, bonding with, or capture by a particle. For example, an agent or drug as disclosed herein can be located on an outer surface of a particle, absorbed within the particle, surrounded by a particle (e.g., within the center of a microcapsule or nanocapsules), and the like. Different compositions can be co-localized in different locations of a particle. For example, a homing agent can be located on an outer surface of a particle to immediately induce monocyte/macrophage homing to an injury site, while a drug can be located within the particle in order to delay release for a desired period of time.

As used herein, the term "co-localized" encompasses the localization of both an agent and a drug on or within the same particle.

As used herein, the term "drug" refers to any substance that is administered with the intention of eliciting a therapeutic effect. The drug may be but is not limited to a small molecule, peptide, protein, antibody, or nucleic acid.

Unless specifically stated or obvious from context, the term "or," as used herein, is understood to be inclusive.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 (as well as fractions thereof unless the context clearly dictates otherwise).

DETAILED DESCRIPTION OF THE INVENTION

The invention is based, in part, on the discovery that monocytes may be exposed to an agent that increases their propensity to home to a site of injury and loaded with a therapeutic payload and which is then carried to a site of injury by the homing action of the monocyte. Once at the site of injury, the therapeutic payload can be released from the monocyte and may exert its therapeutic effect. The agent may also act within the monocyte (or monocyte-derived macrophage), e.g., without being released from the monocyte, in order to affect the monocyte's behavior.

Compositions

In one aspect, the invention provides a composition containing at least one monocyte having an intracellular space containing an agent that increases monocyte homing to a site of injury, and an effective amount of a drug. Some aspects and embodiments do not include the agent that increases monocyte homing to a site of injury. The disclosure below is intended to apply both to embodiments with and without the agent that increases monocyte homing to a site of injury.

The agent and the drug can be separate, separately incorporated within a particle(s), or can be co-localized within the same particle(s). For example, monocytes/macrophages can be exposed to both an agent and a drug either inside or outside of the subject to load the monocytes/macrophages with both substances. Loading of the drug and/or the agent through a particle can be particularly advantageous, especially when the compositions are formed in situ, by delaying release of the drug, some of which may cause off-target side effects.

In various embodiments, the number of monocytes can be varied as necessary to conveniently manufacture the appropriate amount of the composition or to deliver greater or lesser amounts or concentration of the drug. In various embodiments, the monocytes themselves may be from a patient to whom the composition may ultimately be administered, from a donor, or even from various varieties of stem cells. In various embodiments, the monocytes may be prepared in vitro and may be treated to alter monocyte phenotype or behavior. In various embodiments, the major histocompatibility complex (MHC) type is matched between the donor and patient.

In various embodiments, the particle may occupy the intracellular space of the monocyte. The intracellular space refers to the interior of the cell as delineated by the cell membrane. The intracellular space includes compartments within the cell including but not limited to endosomes, lysosomes, and the cytoplasm. In other embodiments, the particle may attach to the surface of the monocyte such that it is carried along as the monocyte travels without entering the monocyte itself.

In various embodiments, the agent that increases monocyte homing to a site of injury may be any compound that increases the propensity of monocytes to migrate towards a site of injury relative to monocytes that have not been exposed to the compound. In various embodiments, the agent that increases monocyte homing may be a chemokine receptor-2 (CCR2) modulator. Without wishing to be bound by theory, modulation of CCR2 may increase binding of monocyte chemoattractant protein-1 (CCL1), and increase the propensity of affected monocytes to migrate toward the site of injury. In various embodiments, the agent that increases monocyte homing may be dexamethasone.

In various embodiments the particle has a maximum cross-sectional dimension (e.g., a diameter of a circular cross-section) between 1 nm and 50 µm (e.g., 10 nm to 20 µm, 10 nm to 200 nm, and the like). The size of the particle influences uptake and release by monocytes and may be varied, as appropriate, in order to facilitate, by way of non-limiting example, efficient loading or specific controlled-release kinetics of drug delivery.

In various embodiments, the particle is a lipid or phospholipid vesicle. The phospholipid vesicle may include one or more concentric lipid layers.

In various embodiments, the particle can be a nanocapsules or microcapsule including a shell (e.g., a polymeric shell) surrounding an inner volume. Exemplary nanocapsules and microcapsule are described in U.S. Patent Application Publication Nos. 2009/0028797, 2012/0109045, and 2014/0213702.

In various embodiments the particle has a hydrophobic polymer core. In various embodiments the hydrophobic polymer is poly(lactic-co-glycolic acid). In various embodiments, the particle comprises a coating. The composition of the particle may be varied as appropriate for the delivery of various drugs, the specific chemical properties of which, such as, but not limited to, solubility and stability, may make various compositions of the particle more or less effective for a given purpose.

In some embodiments, the hydrophobic core or polymeric component is advantageously used in combination with dex. Dex is a small corticosteroid that has a relatively hydrophobic chemical structure, allowing it to be easily adsorbed or conjugated to hydrophobic particles, such as PLGA. The hydrophobic molecule also has the capacity to diffuse through endosomal phospholipid membranes and intracellularly down-regulate inflammatory NFκB pathways as well as stimulate the production of CD163, the iron-sequestering receptor useful in embodiments in which monocyte-derived macrophages clear iron at the site of injury.

In various embodiments, the particle includes one or more cationic polymers. In some embodiments, the cationic polymer may be on the surface of the particle. Various amounts of cationic polymer in combination with other materials or not, may be used to adjust the zeta potential of the nanoparticles. This provides various advantages, including but not limited to tuning particle uptake and release by monocytes.

In various embodiments, the particle includes a targeting ligand. In various embodiments the targeting ligand promotes selective uptake by monocytes. In various embodiments, the targeted ligand includes ligands that engage mannose or scavenger receptors.

In various embodiments, the particle includes a molecule that enhances endosomal escape, such as containing charged polymers or having sharp, jagged, and/or pointed shapes.

In various embodiments the particle includes a fluorescent dye. In some embodiments, the particles may be monitored by following the fluorescence of the dye. Any fluorescent dye may be used and multiple dyes may be used simultaneously for multiplexing applications that may depend on the application of multiple embodiments of the invention targeting overlap regions of the site of injury. In various embodiments the dye may be Nile red, Cy5 or ALEXA FLUOR® 488.

In various embodiments, the drug may be any drug that can be effectively transported and released by monocytes. In some embodiments, the drug affects monocyte or macrophage behavior and may be the same or different than the agent that increases monocyte homing to a site of injury. By way of non-limiting example, the drug may shift the M1/M2 macrophage ratio either up or down, promote unique phenotypes of macrophages, recruit additional monocytes to a site of injury. In various embodiments the drug may be interleukin-4, interleukin-10, interferon-γ or dexamethasone.

In various embodiments the drug affects liver function or health.

In various embodiments, the drug is a prodrug that masks a functional agent and the functional agent is released at the site of injury. A skilled person will appreciate that there are a variety of different prodrug chemistries that may be used to achieve this effect. In some embodiments, monocyte to macrophage or macrophage phenotype changes trigger the unmasking of the active agent from the prodrug.

Methods of Delivering Drugs to a Site of Injury

In another aspect, the invention provides a method of delivering a drug to a site of injury of a patient by administering to the patient a composition comprising at least one monocyte having an intracellular space, including at least one particle including an agent that increases monocyte homing, and an effective amount of a drug, wherein the at least one monocyte travels to the site of injury where the drug is released from the intracellular space, thereby delivering the effective amount of the drug to the site of injury. The embodiments of the composition described above are generally suitable for use in this aspect of the invention.

Once the monocyte reaches the site of injury the drug is released from the intracellular space of the monocyte. In some embodiments, the particle is released from intracellular space, thereby releasing the drug. In various embodiments, this may be triggered by the death of the cell or may take place by passive diffusion. In other embodiments, the particle may dissolve or disintegrate and the drug may exit the cell by passive diffusion. In yet other embodiments the drug diffuses out of the particle and then out of the cell. In these embodiments, the particle may elute into the intracellular space during movement of the cell to the injury site or may remain within the particle until the particle emerges from the cell.

In various embodiments, the release of the drug from the cell may happen in response to biological cues. In various embodiments, the drug is released from the intracellular space by monocyte-to-macrophage differentiation. For example, release may be triggered by proteins or molecules that are upregulated during monocyte-to-macrophage differentiation. In various embodiments the drug may be released in response to increased levels of reactive oxygen species (ROS).

In various embodiments, the site of injury is in the brain of the patient. In certain embodiments, the present method presents the advantage that monocytes can traverse the blood-brain barrier and deliver a drug to the brain. In various embodiments, the drug affects blood-brain barrier integrity or function. By way of non-limiting example, the drug may be methylene blue, mannitol, bradykinin, or serotonin. In various embodiments, the drug promotes neuronal health or stability. By way of non-limiting example, the drug may be P7C3, a brain-derived neurotrophic factor, a nerve growth factor, a calpain inhibitor, or a flavonoid.

The methods of the invention may be applied to target any variety of brain injury capable of attracting monocytes or that monocytes may be induced to travel to. In various embodiments, the injury may be the result of any type of disease or any form of trauma. In various embodiments the injury is a traumatic brain injury.

In various embodiments, the injury may be caused by a disease associated with the misfolding and aggregation of endogenous proteins. In various embodiments, the injury may be the result of a disease associated with the aggregation of α-synuclein, i.e., a synucleopathic disease. In various embodiments, the synucleopathic disease is Parkinson's disease or dementia with Lewy bodies. In various embodiments, the injury is a lesion caused by an amyloid-β-mediated disease. In various embodiments, the amyloid-β mediated-disease is Alzheimer's disease.

In various embodiments, techniques may be used to induce monocyte homing to the site of injury, in addition to or as an alternative to chemical agents. In various embodiments, the particles may include iron oxides or other paramagnetic materials and a magnetic field may be applied to the body of the patient, inducing monocytes to travel to or accumulate at the site of injury or enabling imaging through magnetic resonance.

In various embodiments, techniques may be used to alter or induce drug release. In some embodiments, the particle has an interior space containing the drug, i.e., is a capsule. In various embodiments, a mechanical or chemical signal ruptures the capsule and releases the drug, either within the intracellular space of the monocyte or not. In various embodiments, ultrasound is applied to the site of injury causing the capsule to cavitate and rupture.

The monocytes need not be prepared in vitro and endogenous monocytes may be hijacked and used for drug transport to a site of injury. In another aspect, the invention provides a method of delivering a drug to a site of an injury in a patient by administering to the patient (e.g., intravenously, parenterally, orally, and the like) particles including an agent that increases monocyte homing and an effective amount of a drug. The particles enter at least one endogenous monocyte. The endogenous monocyte travels to the site of injury in the patient and the particle is released from the monocyte, thereby delivering the effective amount of the drug to the site of injury.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

Example 1: Particles are Stable in the Intracellular Space of Macrophages Over Time In order to test if monocyte-derived macrophages (MDM) can be reprogrammed and used as a therapeutic following traumatic brain injury (TBI), polymeric microparticles that can promote and maintain an anti-inflammatory MDM phenotype were fabricated. After administering different types of polymeric particles to MDM, it was determined that poly(lactic-co-glycolic acid) (PLGA) microparticles loaded with a model drug were detectable intracellularly for more than two weeks and slowly released drug to the cell's cytoplasm over that time frame.

To test if intracellular PLGA particles were capable of preserving a drug's bioactivity, PLGA particles loaded with dexamethasone (DEX) were fabricated because DEX is anti-inflammatory, promotes phagocytosis, crosses membranes, and has cytoplasmic receptors. After introducing DEX-loaded particles to MDM, particles were rapidly phagocytosed, stored intracellularly, and released DEX intracellularly to direct MDM behavior. MDM loaded with particles upregulated the phagocytic receptors for one week in vitro relative to untreated MDM, suggesting that released DEX altered MDM behavior. To examine if particles could prevent MDM inflammatory polarization even in the presence of pro-inflammatory stimuli, particles were fabricated with increasing amounts of DEX and administered to MDM. Subsequent treatment with inflammatory stimuli precluded inflammatory polarization for up to one week in vitro in the cells treated with the highest DEX-loaded particles. Finally, cells treated with DEX particles upregulated phagocytosis of myelin debris, even in the presence of inflammatory stimuli.

This work suggests that exogenously loading MDM with polymeric particles can generate and maintain anti-inflammatory MDM behavior even in the presence of inflammatory stimuli.

This project employs innovative drug delivery techniques to harness endogenous repair systems to improve recovery after TBI. However, persistent inflammation is a problem in many diseases and disorders including multiple sclerosis, stroke, epilepsy, Alzheimer's disease, amyotrophic lateral sclerosis, spinal cord injury, myocardial infarction, and chronic wounds, among others. Because of the ubiquitous nature of macrophage involvement in driving inflammation, research aimed to elucidate mechanisms of inflammation and simultaneously investigate methods of redirecting inflammation to promote regeneration could inform therapeutic intervention strategies across a wide spectrum of neurological and peripheral disorders.

TBI affects a large global population every year, but despite the devastating consequences of neurological trauma and researchers' efforts, therapeutic interventions to help retain neurological function and prevent neuronal loss remain elusive. Here, an engineering approach was utilized to investigate the innate immune system's capacity to mitigate neuroinflammation and rescue mechanically damaged neurons following TBI. Utilizing this approach, MDM loaded with anti-inflammatory particles can home to the brain, modulate inflammation, and promote clearance of toxic cellular debris. This may lead to a better understanding of the innate immune system's role in neurodegeneration by redirecting potentially neurotoxic behaviors of MDM. Exploration of this platform may lead to improved nervous system repair and a better understanding of neurobiology after trauma.

Figure 2A:
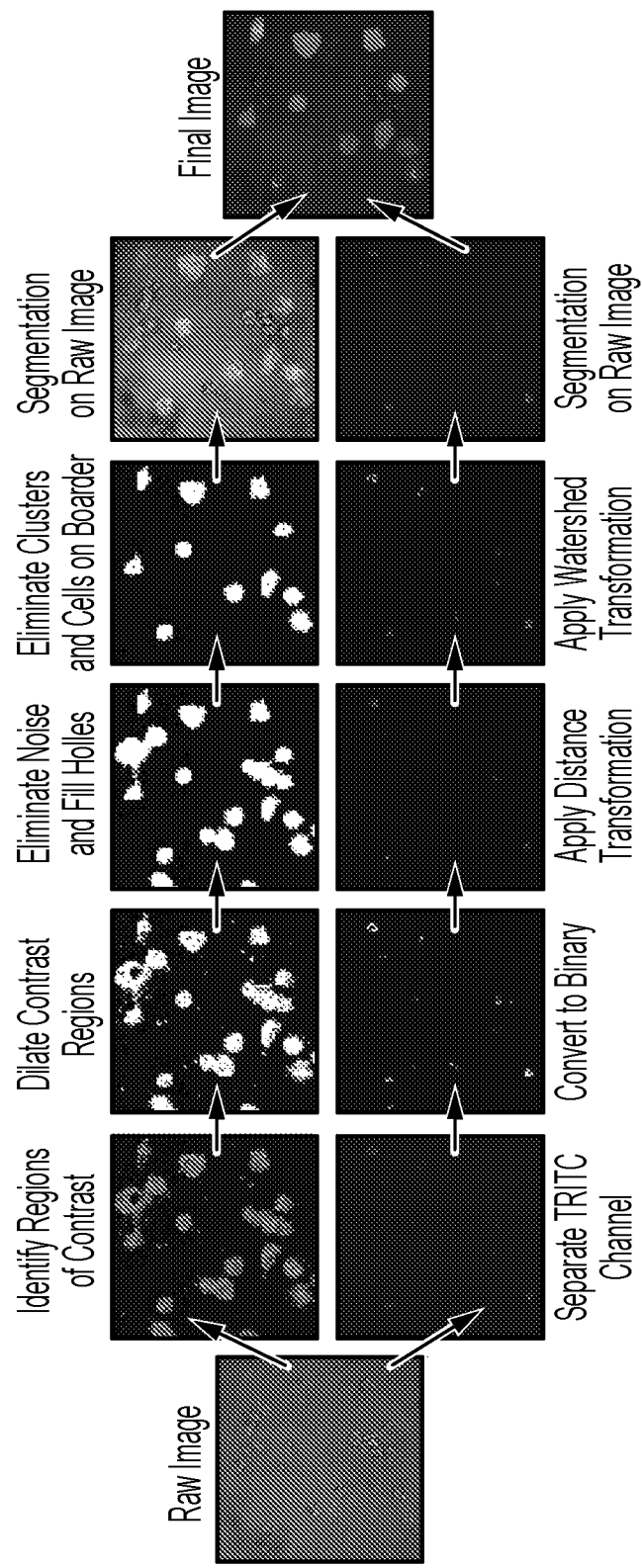
FIG. 2A depicts custom MATLAB® code steps to complete feature-based segmentation on confocal images.

To test the stability of PLGA particles following phagocytosis by MDM, particles loaded with the model drug tetramethylrhodamine (TRITC) were fabricated. Thereafter, particles were administered to human primary MDM at a concentration of 20 µg of particles per million cells. Cells were allowed to incubate with particles for four hours to facilitate particle uptake by monocytes. Thereafter, cells were washed to remove any non-phagocytosed particles and plated in complete media supplemented with macrophage colony stimulating factor (MCSF). Cells were imaged at regular intervals over 21 days to characterize particle longevity inside cells. Images were acquired with an OLYMPUS® confocal microscope to capture differential interference contrast channel and the fluorescent TRITC channel. In order to quantify particle longevity inside cells over time a novel MATLAB® script was generated in order to complete feature-based segmentation image processing (FIG. 2A). In brief, the differential interference contrast channel was isolated, converted to binary, regions of high contrast were identified, and these pixels were dilated. Thereafter, small noise was eliminated, holes inside objects were filled, and cells on the border of the image and in clusters of cells were removed to prevent any data skewing. The cell segmentation was then applied on top of the raw image to validate accurate cell segmentation. In parallel, the TRITC channel was isolated, converted to binary, a distance transform was applied in order to segment objects according to a Watershed Transform. The particle segmentation was then applied on top of the raw image to validate accurate particle segmentation (FIG. 2A). Once segmentation for each image was complete, cell size, number of particles per cell, particle intensity, and total drug loading per cell was extracted.

Figure 2B:
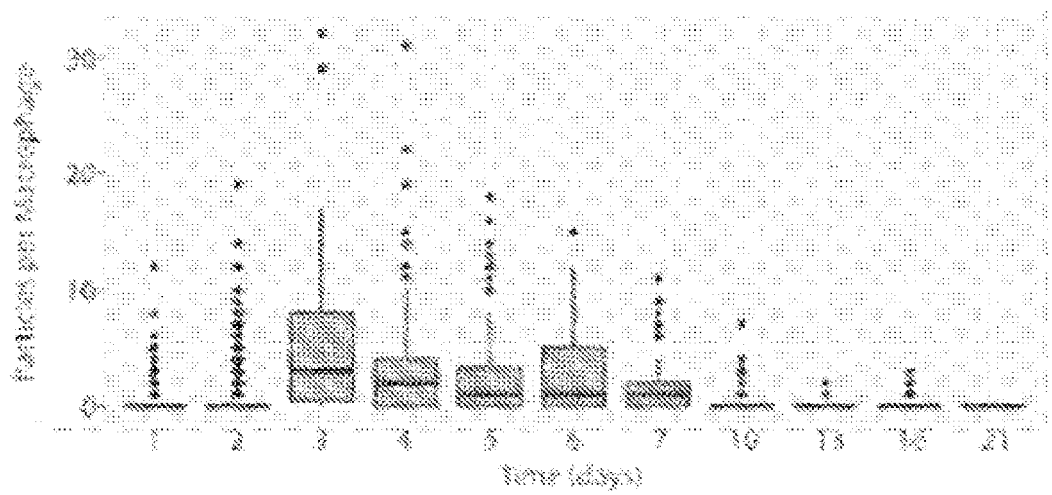
FIG. 2B-2D depict intracellular particle number (FIG. 2B), intensity (FIG. 2C), and total drug loading (FIG. 2D) inside macrophages over time.
Figure 2C:
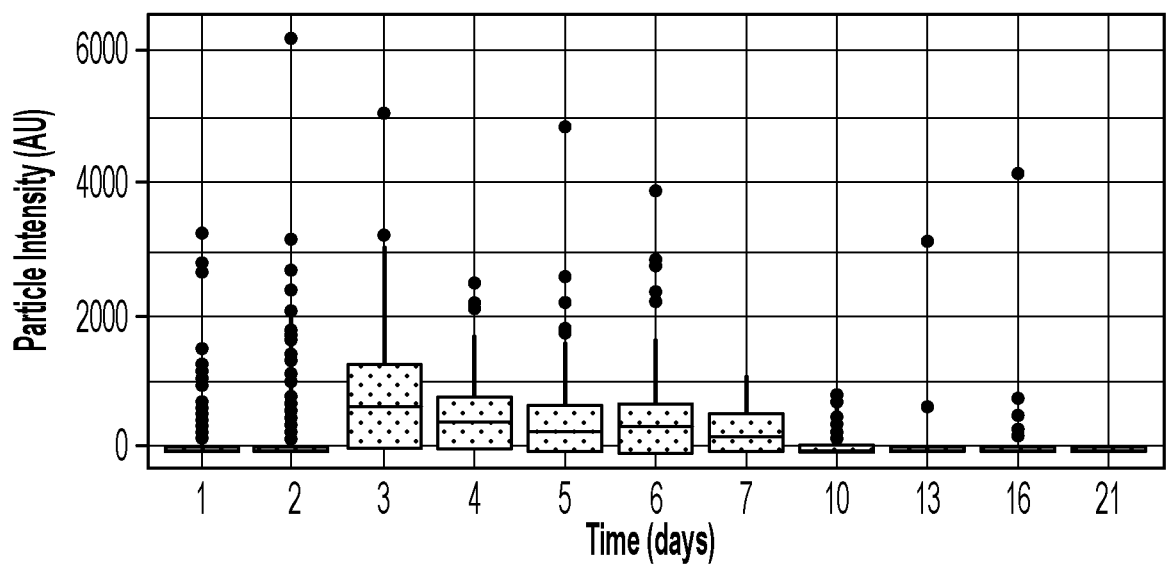
Figure 2D:
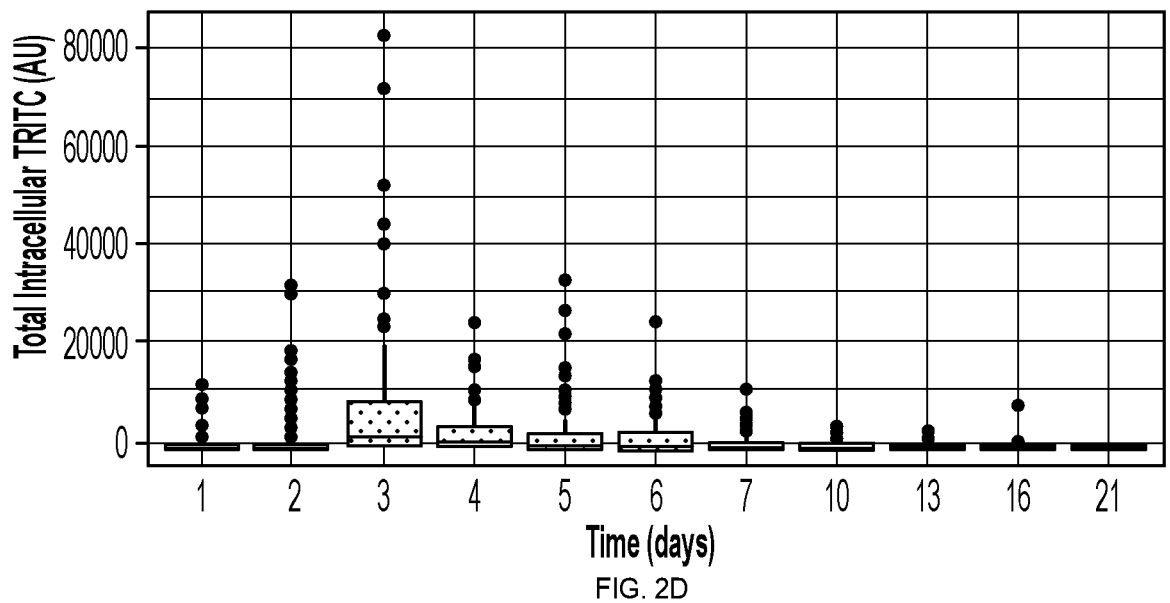
Figure 3:
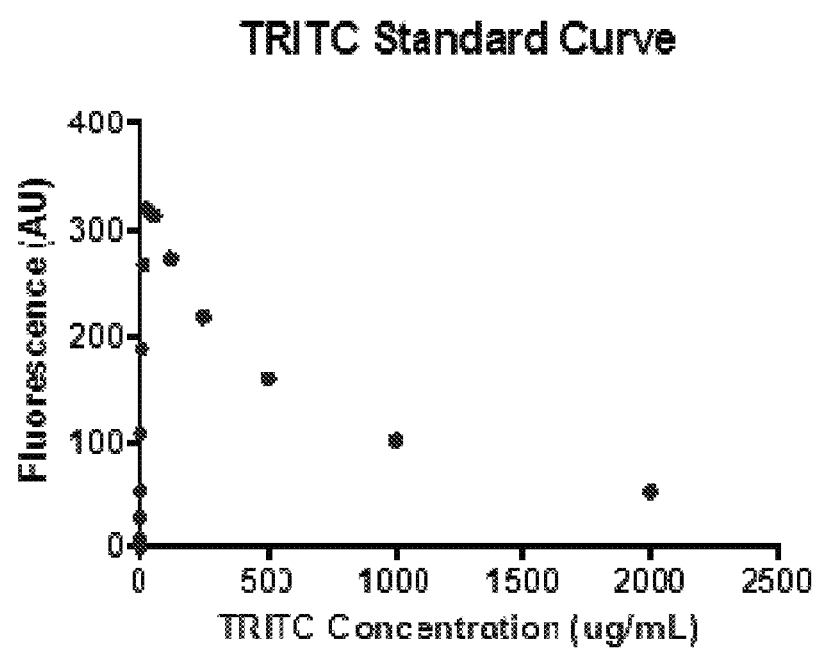
FIG. 3 is a chart showing that tetramethylrhodamine (TRITC) exhibits rhodamine-to-rhodamine quenching. TRITC concentration below 31 ug mL$^{-1}$ is directly proportional to fluorescence. However, TRITC concentration above 31 ug mL$^{-1}$ results in decreased fluorescence.
Figure 4:
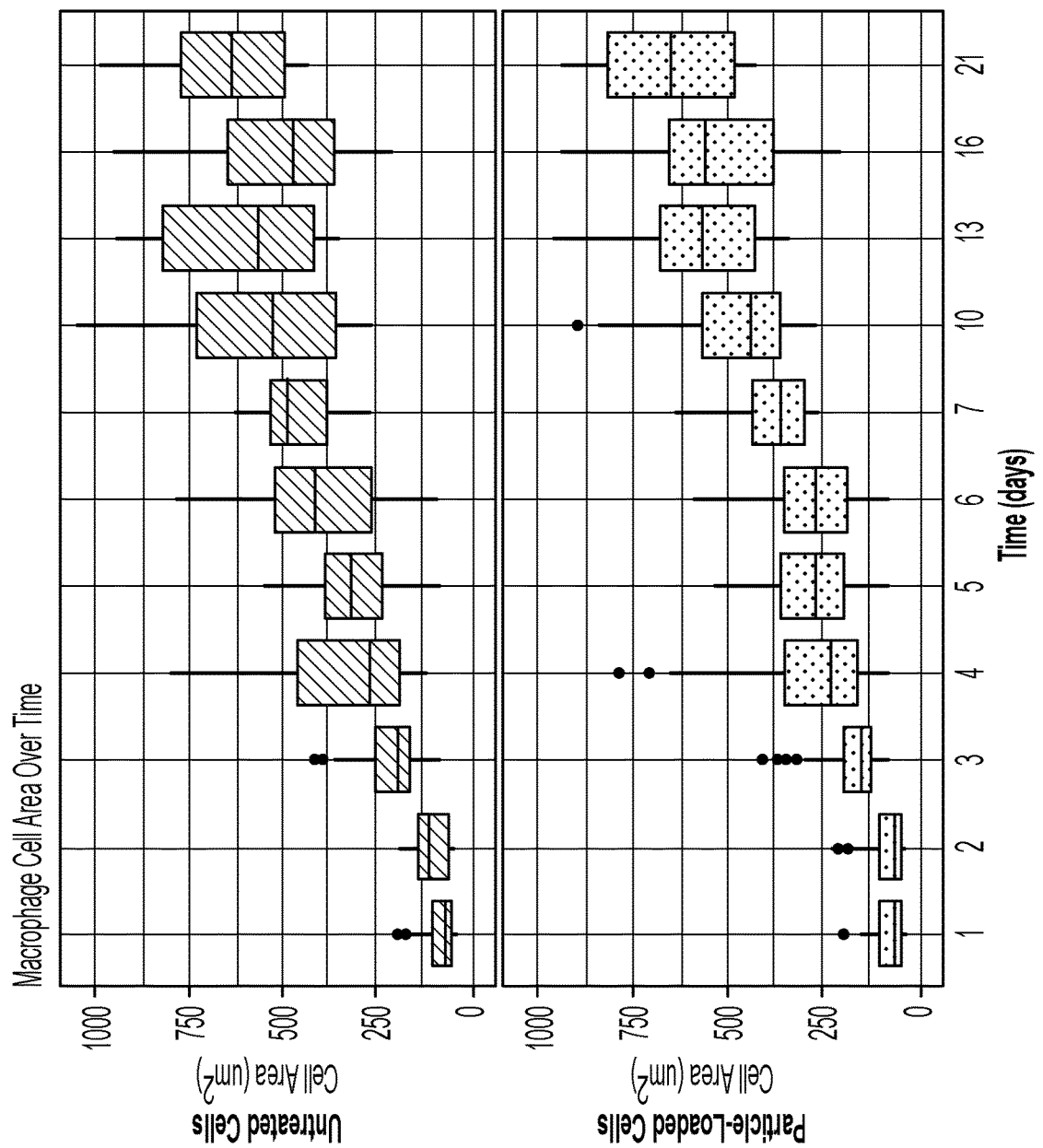
FIG. 4 shows that loading monocyte-derived macrophages (MDM) with particles does not interfere with cell spreading over time, a characteristic of monocyte to macrophage differentiation. Cells that were untreated (top graph) spread to a similar extent as particle-loaded cells (bottom graph).

An increase in particle number, particle intensity, and total drug loading (defined as the number of particles multiplied by the particle intensity per cell) was observed up until day 3, followed by a decrease in all three metrics thereafter (FIGS. 2B-D). Importantly, data from day 1 and day 2 may underrepresent the number of intracellular particles and their intensities because TRITC exhibits rhodamine-to-rhodamine quenching, where increasing concentration of TRITC correlates to an increase in fluorescence up until 31 ug mL-1 (FIG. 3). Thereafter, any subsequent increase in TRITC concentration correlates with a decrease in TRITC fluorescence (FIG. 3). Because of this quenching behavior, there may be many particles with high TRITC loading that are not fluorescently detectable at early time points. Additionally, it was observed that phagocytosis of particles did not interfere with monocyte differentiation into macrophages because cell spreading over time was conserved in particle-loaded and untreated macrophage conditions (FIG. 4).

Example 2: Intracellular Particles Release Model Drugs, which Localize with Cytoplasmic Receptors The particle longevity data suggests that the PLGA particles are durable enough to survive intracellularly for over two weeks. However, it is important to test if particles were able to release drugs to the cytoplasm of cells. Cytoplasmic delivery of molecules is important because the cytoplasm houses a vast number of molecules that could be regulated by therapeutics. In order to test if a drug could be delivered to the cytoplasm, PLGA particles loaded with the model drug TRITC were utilized. Particles were administered to cells for four hours and any non-phagocytosed particles were removed from the system. After five days, the cells were fixed and stained with the cytoplasmic, glucocorticoid receptor BuGR2. Following immunocytochemical staining, the cells were imaged on an OLYMPUS® confocal microscope. Signal for nuclei (DAPI, FIGS. 5A and 5D), particles (TRITC, FIGS. 5B and 5D), and the cytoplasm marker (BuGR2, FIGS. 5C and 5D) were evident. To investigate if the TRITC signal co-localized with the cytoplasmic signal, BuGR2 signal was pseudocolored to green, TRITC signal was expressed as red, and regions of overlap were expressed as white pixels (FIGS. 5E and 5F). Many white pixels in the zoomed-in, pseudo-colored image suggests that TRITC was able to leave the particle, enter the cytoplasm, and co-localize with BuGR2. Additionally, co-localization of this stain was important because BuGR2 is a glucocorticoid receptor and the first therapeutic drug of interest, dexamethasone, is a glucocorticoid.

Figure 6:
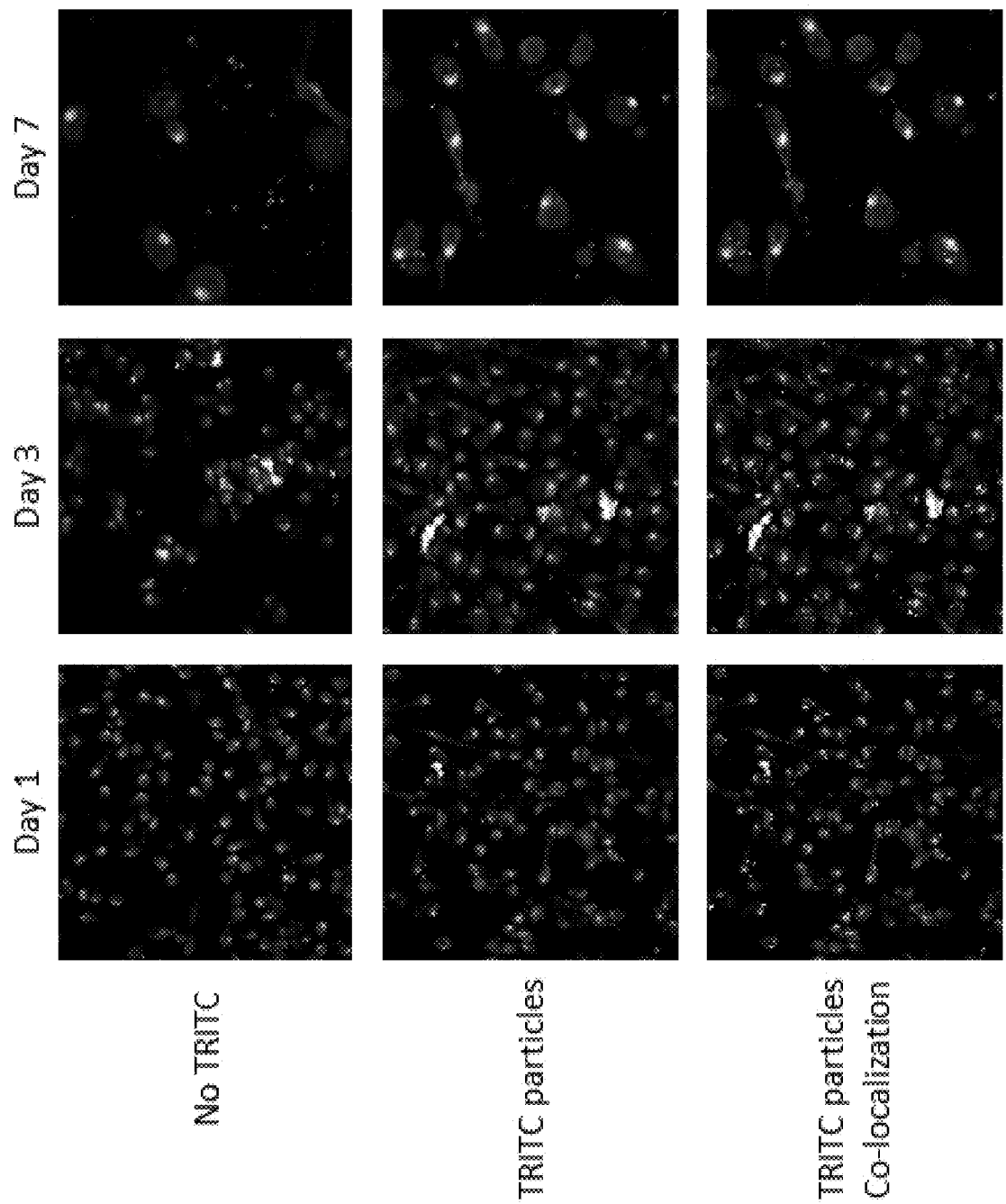
FIG. 6 shows that TRITC signal co-localized with BuGR2 signal at one, three, and seven days after particle administration. Cellular nuclei, human glucocorticoid receptor, TRITC particles, and the cytoplasmic receptor BuGR are expressed on all particle-loaded macrophages. White pixels in the bottom row indicate co-localization between TRITC and BuGR2.
Figure 7:
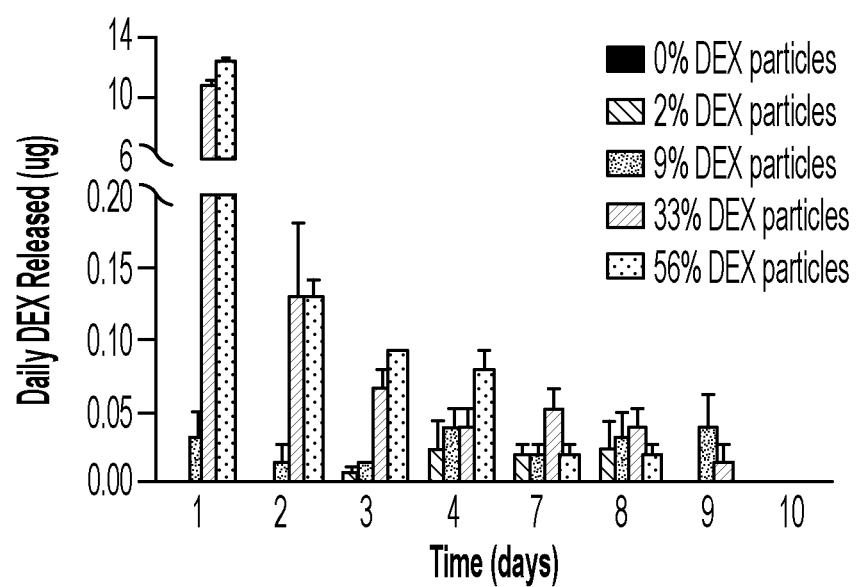
FIG. 7 is a chart showing release of DEX from particles that were fabricated with increasing loading of DEX, ranging from 0% w/w to 56% w/w particles. Release of DEX from particles into 1× PBS showed a large burst release for particles with high DEX loading. DEX release was detectable out until day 9 for most particles.
Figure 8:
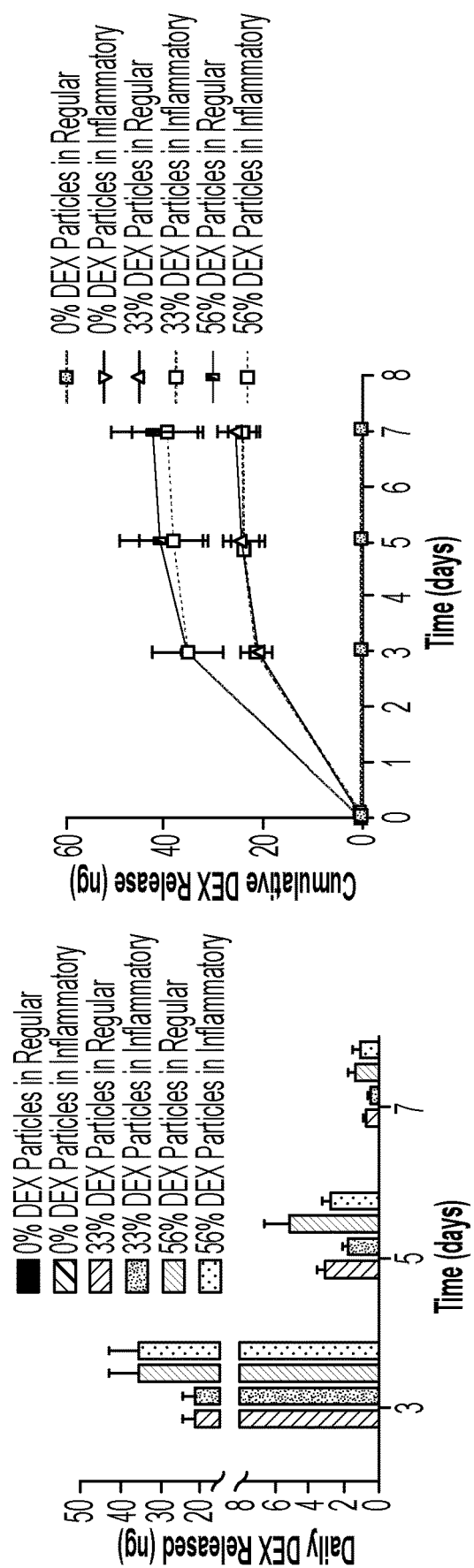
FIG. 8 depicts release of DEX into the extracellular space from cells containing DEX particles in their intracellular space. DEX was detectable in the extracellular space for seven days after particle administration.
Figure 10:
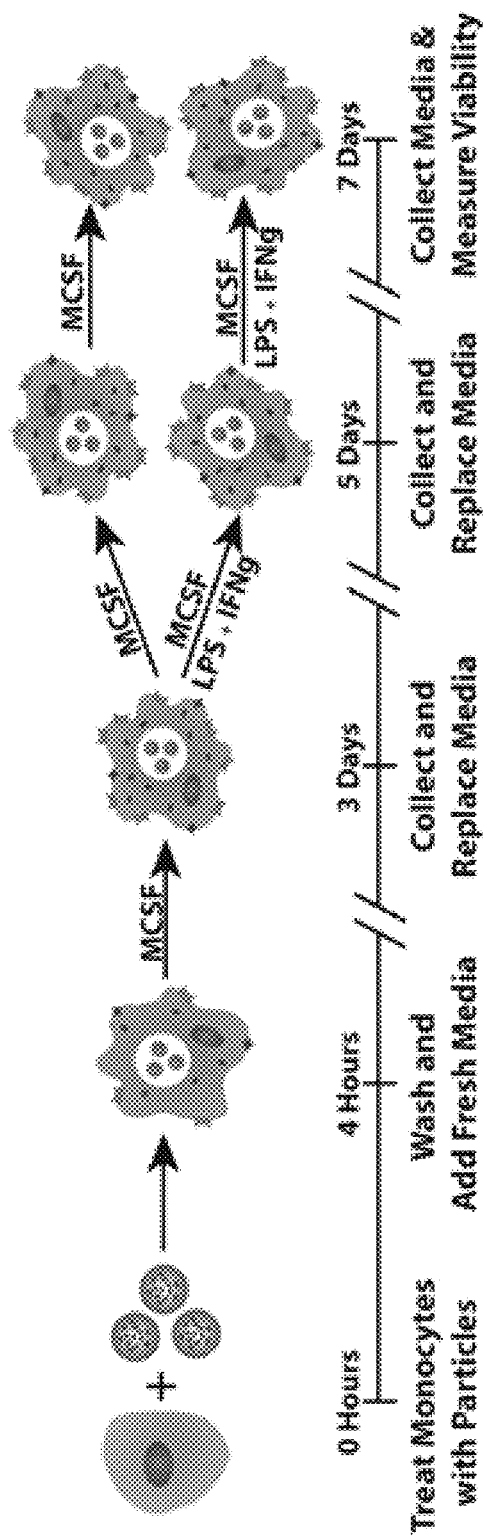
FIG. 10 is a schematic of the experimental paradigm to test particles' efficacy in directing phenotype in the presence of inflammatory stimuli. Particle-loaded MDM were cultured for seven days in either regular media or inflammatory media. After seven days the conditioned media was collected and analyzed for inflammatory protein production.
Figure 11:
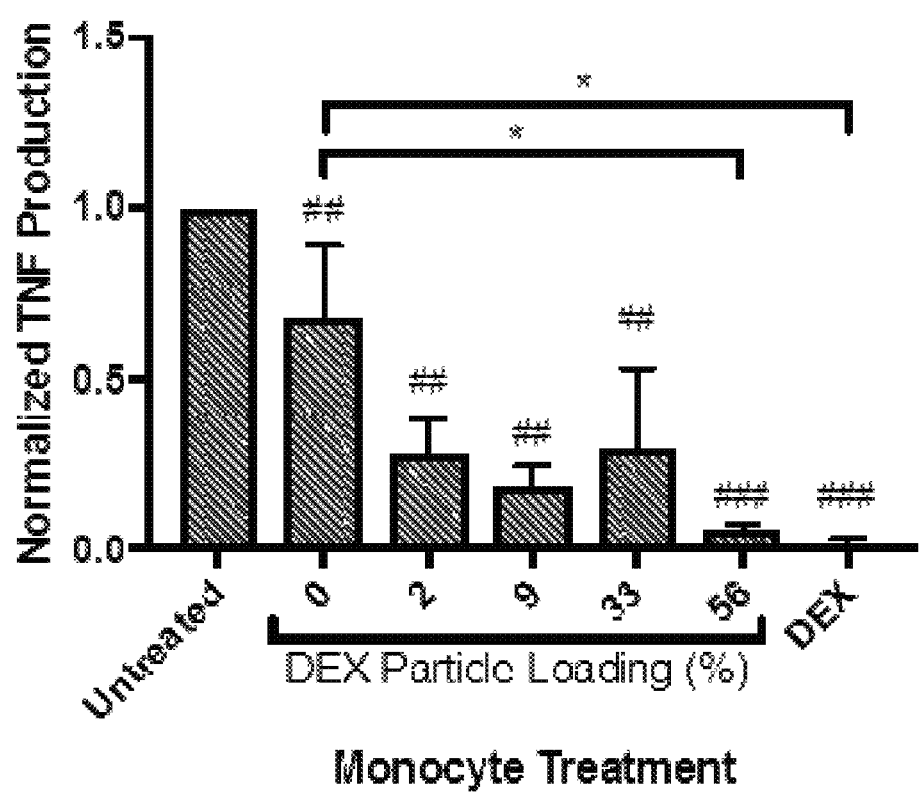
FIG. 11 depicts TNF protein production from particle-loaded macrophages after seven days in vitro. Increasing DEX loading in intracellular particles was inversely correlated with inflammatory protein production.
Figure 12:
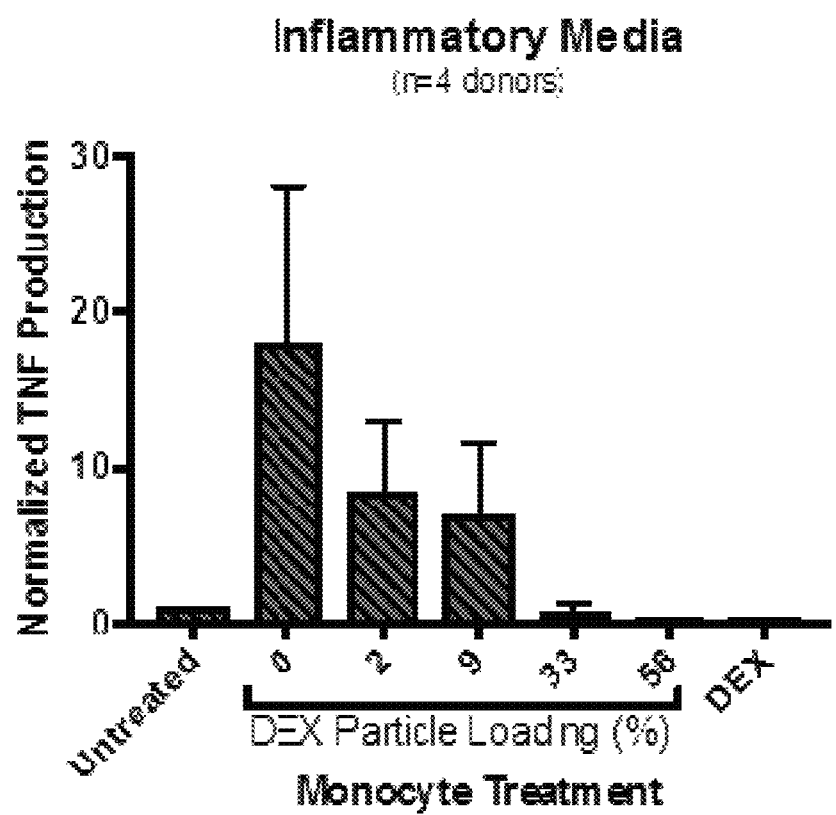
FIG. 12 depicts TNF protein production from MDM collected from four different human donors after seven days in vitro. Increasing DEX loading in particles inversely correlated with inflammatory protein production across all human donors.
Figure 13:
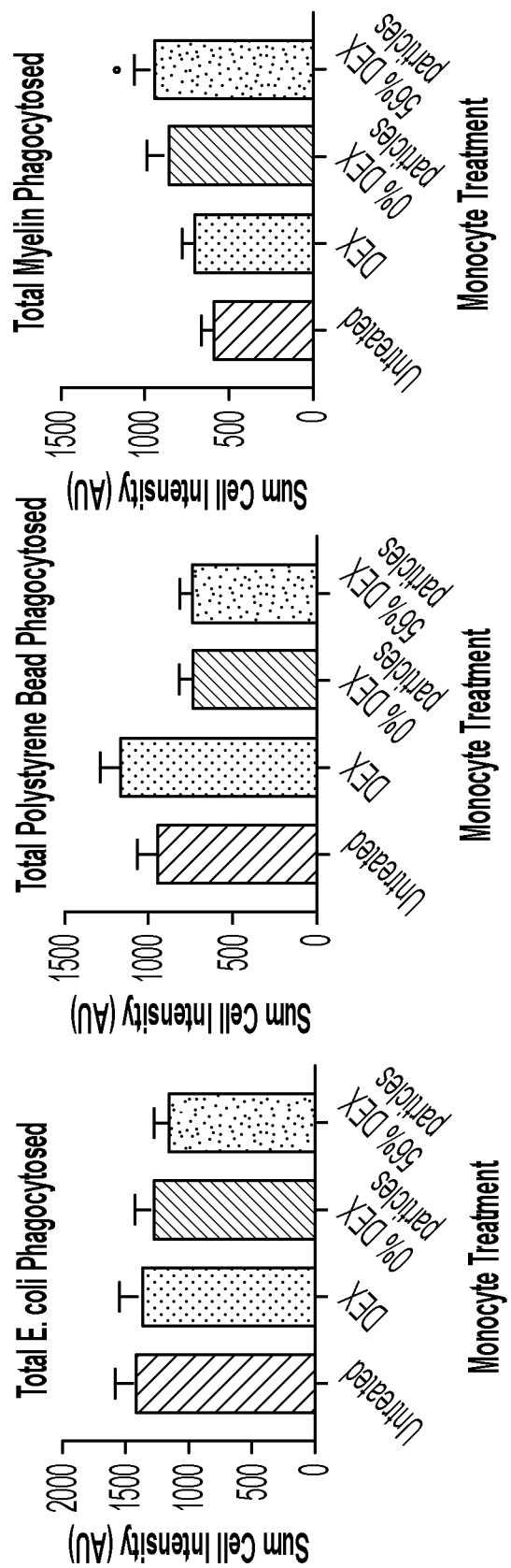
FIG. 13 shows that particle-loaded macrophages preserved their capacity to phagocytose objects including *E. coli*, polystyrene beads, and myelin. Importantly, pre-treatment of monocytes with DEX particles significantly increased myelin uptake in the particle-loaded cells.
Figure 14:
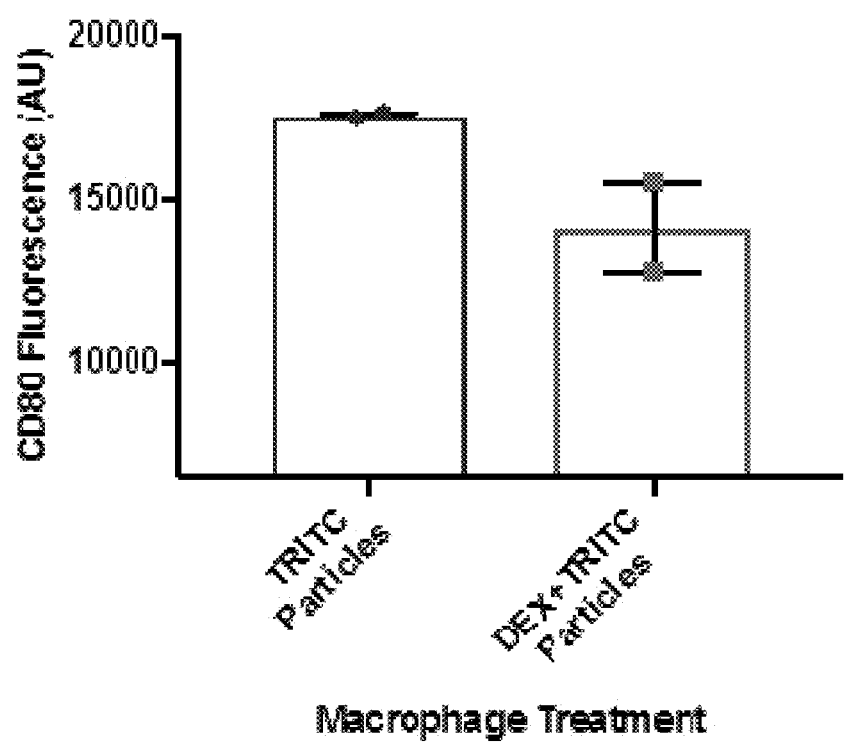
FIG. 14 is a bar graph showing that DEX-loaded particles can modulate and maintain phenotype in murine macrophages over time. CD80 surface expression, indicative of inflammation, was downregulated in murine macrophages five days after treatment with DEX particles.

Repeating the study with multiple time points yielded similar results, where BuGR2 signal and TRITC signal co-localized in the cells (indicated with white pixels) over the first seven days following particle administration (FIG. 6).

EQUIVALENTS

Although preferred embodiments of the invention have been described using specific terms, such description is for illustrative purposes only, and it is to be understood that changes and variations may be made without departing from the spirit or scope of the following claims.

INCORPORATION BY REFERENCE

The entire contents of all patents, published patent applications, and other references cited herein are hereby expressly incorporated herein in their entireties by reference.

The invention claimed is:

1. A composition comprising at least one monocyte comprising:
   an agent that increases monocyte homing to a site of injury, wherein the agent that increases monocyte homing is a CCR2 modulator, and
   an effective amount of a drug.

2. The composition of claim 1, wherein one or more of the agent and the drug are localized within one or more particles within the monocyte.

3. The composition of claim 2, wherein the particle has a cross-sectional dimension between 1 nm and 50 μm.

4. The composition of claim 2, wherein the particle comprises a cationic polymer.

5. The composition of claim 2, wherein the particle comprises a hydrophobic polymer core.

6. The composition according to claim 5, wherein the hydrophobic polymer core comprises a poly(lactic-co-glycolic acid).

7. A composition comprising at least one monocyte comprising:
   an agent that increases monocyte homing to a site of injury, wherein the agent that increases monocyte homing is dexamethasone, and
   an effective amount of a drug.

8. The composition according to claim 7, wherein one or more of the agent and the drug are localized within one or more particles within the monocyte.

9. The composition according to claim 8, wherein the particle has a cross-sectional dimension between 1 nm and 50 μm.

10. The composition according to claim 8, wherein the particle comprises a cationic polymer.

11. The composition according to claim 8, wherein the particle comprises a hydrophobic polymer core.

12. The composition according to claim 11, wherein the hydrophobic polymer core comprises a poly(lactic-co-glycolic acid).

* * * * *